US008917315B2

(12) United States Patent
Negishi

(10) Patent No.: US 8,917,315 B2
(45) Date of Patent: Dec. 23, 2014

(54) IMAGING MODULE

(71) Applicant: Olympus Corporation, Tokyo (JP)

(72) Inventor: Nau Negishi, Yokohama (JP)

(73) Assignee: Olympus Corporation, Tokyo (JP)

( * ) Notice: Subject to any disclaimer, the term of this patent is extended or adjusted under 35 U.S.C. 154(b) by 70 days.

(21) Appl. No.: 13/667,496

(22) Filed: Nov. 2, 2012

(65) Prior Publication Data

US 2013/0120647 A1    May 16, 2013

Related U.S. Application Data

(63) Continuation of application No. PCT/JP2011/060530, filed on May 2, 2011.

(30) Foreign Application Priority Data

May 7, 2010    (JP) .................................. 2010-107323

(51) Int. Cl.
*H04N 13/00*    (2006.01)
(Continued)

(52) U.S. Cl.
CPC .......... *H04N 5/2254* (2013.01); *G02B 23/2423* (2013.01); *G02B 7/022* (2013.01); *A61B 1/04* (2013.01); *G02B 23/2484* (2013.01); *G02B 7/1805* (2013.01); *H04N 2005/2255* (2013.01); *H04N 5/2257* (2013.01); *A61B 1/00057* (2013.01); *G03B 17/17* (2013.01)
USPC ........................................... 348/45; 348/373

(58) Field of Classification Search
CPC ................. H04N 2005/2255; H04N 13/0296; H04N 13/0055; A61B 1/05; A61B 1/042; A61B 1/045; A61B 1/00036; A61B 1/0005; A61B 19/52
USPC ........................ 348/45, 65, 77, 72, 373–375
See application file for complete search history.

(56) References Cited

U.S. PATENT DOCUMENTS 6,351,612 B1 * 2/2002 Misawa ........................ 396/287
6,707,619 B1 * 3/2004 Okuno .......................... 359/694
(Continued)

FOREIGN PATENT DOCUMENTS

| CN | 101164495 A | 4/2008 |
|----|-------------|--------|
| JP | S59-129050 A | 7/1984 |

(Continued)

OTHER PUBLICATIONS

International Search Report dated Aug. 9, 2011 issued in PCT/JP2011/060530.

(Continued)

*Primary Examiner* — Daniel M Pasiewicz
*Assistant Examiner* — Selam Gebriel
(74) *Attorney, Agent, or Firm* — Scully, Scott, Murphy & Presser, P.C.

(57) ABSTRACT

An imaging module includes: a hollow lens holder open at both ends; a lens assembled in the lens holder and collecting light input from one end of the lens holder; a hollow imaging holder having an opening into which the light output from the lens is input; an optical member assembled in the imaging holder and transmitting or deflecting the light input from one end of the imaging holder; and an image sensor assembled in the imaging holder and having a light-receiving region configured to receive the light transmitted or deflected by the optical member and to perform photoelectric conversion of the received light, wherein an optical axis center of the lens and a center of the light received by the light-receiving region of the image sensor are aligned with each other by fitting a light-output-side end portion of the lens holder and the imaging holder to each other.

4 Claims, 12 Drawing Sheets

(51) Int. Cl.
*H04N 5/225* (2006.01)
*G02B 23/24* (2006.01)
*G02B 7/02* (2006.01)
*A61B 1/04* (2006.01)
*G02B 7/18* (2006.01)
*A61B 1/00* (2006.01)
*G03B 17/17* (2006.01)

(56) References Cited

U.S. PATENT DOCUMENTS

| | | | |
|---|---|---|---|
| 7,878,971 B2 * | 2/2011 | Nishimura et al. | 600/117 |
| 8,167,792 B2 * | 5/2012 | Tanaka | 600/117 |
| 8,217,646 B2 * | 7/2012 | Karpen | 324/228 |
| 2005/0078175 A1 * | 4/2005 | Kaneko | 348/65 |
| 2005/0157168 A1 * | 7/2005 | Kaneko | 348/72 |
| 2006/0061891 A1 | 3/2006 | Ito et al. | |
| 2006/0139637 A1 | 6/2006 | Cho et al. | |
| 2008/0088701 A1 * | 4/2008 | Unsai et al. | 348/65 |
| 2010/0220990 A1 * | 9/2010 | Tsujiyama | 396/260 |

FOREIGN PATENT DOCUMENTS

| | | |
|---|---|---|
| JP | S61-55710 A | 3/1986 |
| JP | 62066220 A | 3/1987 |
| JP | 08-106055 | 4/1996 |
| JP | 11-352413 | 12/1999 |
| JP | 2002131656 A | 5/2002 |
| JP | 2005095432 A | 4/2005 |
| JP | 2005-287936 A | 10/2005 |
| JP | 2005-300690 | 10/2005 |
| JP | 2006-15076 A | 1/2006 |
| JP | 2006-119573 | 5/2006 |
| JP | 2006-178472 | 7/2006 |
| WO | WO 2008/084646 A1 | 7/2008 |

OTHER PUBLICATIONS

Japanese Office Action dated Apr. 22, 2014 issued in corresponding Application No. 2010-107323 together with an English language translation.

Notice of Rejection dated Jul. 15, 2014 from related Japanese Patent Application No. 2010-107323, together with an English language translation.

* cited by examiner (1)

(2)

(1)

(2)

IMAGING MODULE

CROSS-REFERENCE TO RELATED APPLICATIONS

This application is a continuation of PCT international application Ser. No. PCT/JP2011/060530 filed on May 2, 2011 which designates the United States, incorporated herein by reference, and which claims the benefit of priority from Japanese Patent Application No. 2010-107323, filed on May 7, 2010, incorporated herein by reference.

BACKGROUND OF THE INVENTION

1. Field of the Invention

The present invention relates to an imaging module including an image sensor and an optical member.

2. Description of the Related Art

Conventionally, various types of electronic imaging apparatus such as a digital camera, a video camera, an endoscope apparatus for observing an interior of an organ of a subject, and a mobile phone device having an imaging function have appeared. Among them, in the endoscope apparatus, an imaging module that mounts an image sensor is built in a distal end portion of a long and narrow insertion tool having flexibility. The endoscope apparatus is capable of observing a region to be observed or the like by inserting the insertion tool into a body cavity.

The imaging module has the image sensor built in, such as a CCD or a CMOS image sensor, images an optical image of an object on a light-receiving region of the image sensor by an optical system such as a lens, and captures image data of the object by photoelectric conversion processing by the image sensor.

Here, to relieve a burden on the subject or the like, it has been desired to downsize the diameter of the distal end of the insertion tool in the endoscope apparatus. In recent years, an imaging module has been proposed wherein a prism is placed on an image sensor arranged approximately parallel with an optical axis of an objective lens system in order to secure a sufficient light-receiving area on the image sensor even in a case where the area of a vertical surface with respect to the optical axis that can be used for the imaging module becomes small due to the downsizing of the diameter of the distal end of the insertion tool (for example, see Japanese Patent Application Laid-open No. 8-106055).

SUMMARY OF THE INVENTION

An imaging module according to an aspect of the present invention includes: a hollow lens holder open at both ends; a lens assembled in the lens holder and collecting light input from one end of the lens holder; a hollow imaging holder having an opening into which the light output from the lens is input; an optical member assembled in the imaging holder and transmitting or deflecting the light input from one end of the imaging holder; and an image sensor assembled in the imaging holder and having a light-receiving region formed on a surface, the light-receiving region being configured to receive the light transmitted or deflected by the optical member and to perform photoelectric conversion of the received light, wherein an optical axis center of the lens and a center of the light to be received by the light-receiving region of the image sensor are aligned with each other by fitting a light-output-side end portion of the lens holder and the imaging holder to each other.

The above and other features, advantages and technical and industrial significance of this invention will be better understood by reading the following detailed description of presently preferred embodiments of the invention, when considered in connection with the accompanying drawings.

DETAILED DESCRIPTION OF THE PREFERRED EMBODIMENTS

An imaging module built in a distal end of an insertion tool of an endoscope apparatus will be exemplarily described in detail as an imaging module according to Embodiments of the present invention with reference to the appended drawings. Note that the present invention is not limited to Embodiments. Further, the substantially same elements are denoted with the same reference signs. Further, note that the drawings are schematically shown, and the relation between the thickness and the width of each member, a ratio of each member and the like are different from reality. Also, some parts having a difference in mutual size relation or ratio are contained between the drawings.

(First Embodiment)

Figure 1:
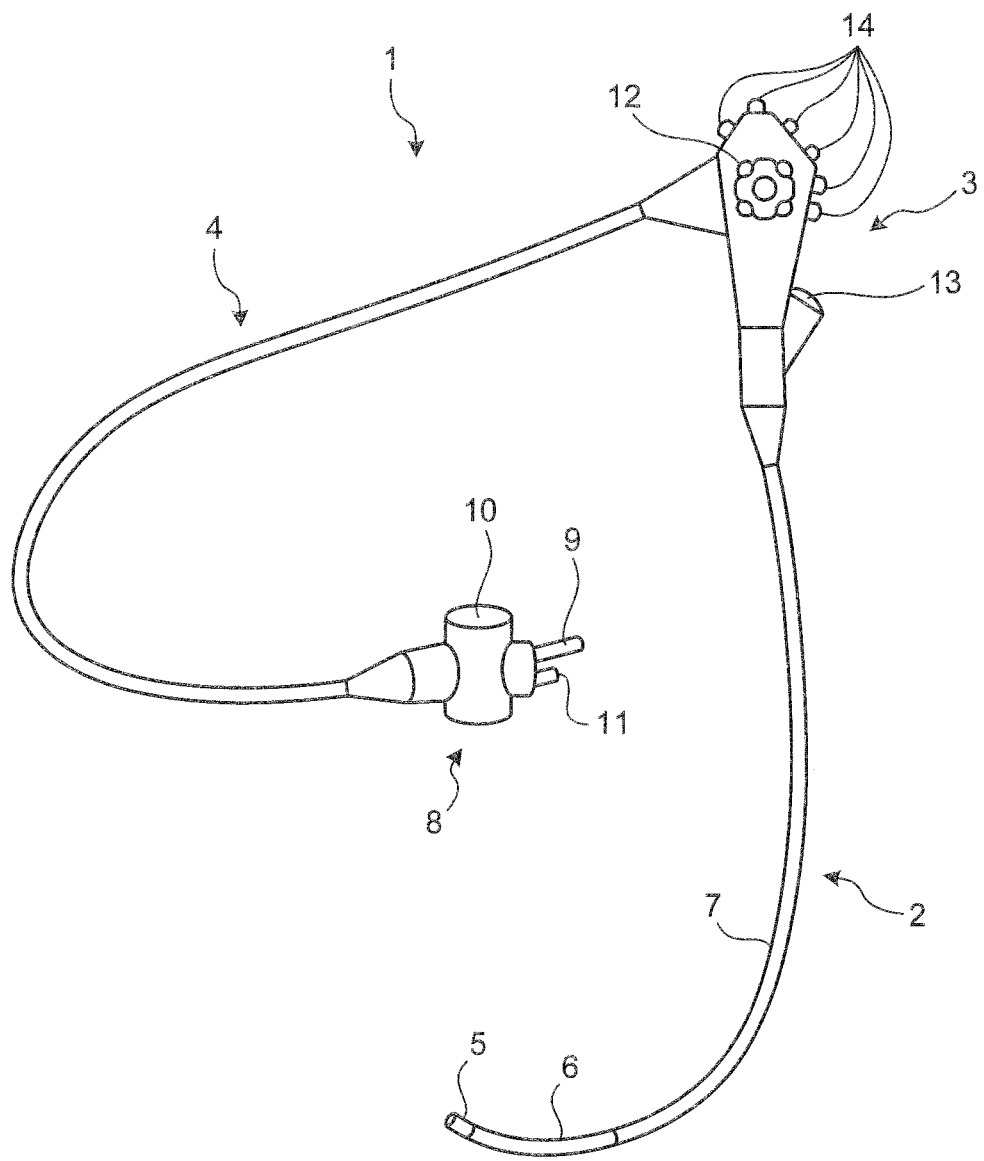
FIG. 1 is a schematic diagram showing a configuration of an endoscope apparatus according to a first embodiment.

First, an endoscope apparatus according to a first embodiment will be described. FIG. 1 is a diagram showing an outline configuration of the endoscope apparatus according to the first embodiment. As shown in FIG. 1, an endoscope apparatus 1 according to the first embodiment includes a long and narrow insertion unit 2, an operating unit 3 at a proximal end side of the insertion unit 2 and held by an operator of the endoscope apparatus, and a flexible universal cord 4 extending from a side portion of the operating unit 3. The universal cord 4 is equipped with a light guide cable, an electrical cable, and the like.

The insertion unit 2 includes a distal end part 5 having an imaging module built-in, the imaging module having an image sensor such as a CCD, a freely bendable bending part 6 formed by a plurality of bending pieces, and a long flexible tube part 7 having flexibility and provided at a proximal end side of the bending part 6.

A connector unit 8 is provided at an end portion of an extending side of the universal cord 4. The connector unit 8 includes a light guide connector 9 detachably connected to a light source device, an electrical connection part 10 for transmitting an electrical signal of an object image subjected to photoelectric conversion by a CCD or the like to a signal processing device or a control device, an air-supplying ferrule 11 for supplying air to a nozzle at the distal end part 5, and the like. Note that the light source device is equipped with a halogen lamp and the like, and supplies the light from the halogen lamp to the endoscope apparatus 1 via the light guide connector 9 as illumination light. Further, the signal processing device and the control device are devices that supply a power source to the image sensor, and into which the electrical signal subjected to the photoelectric conversion is input from the image sensor. The signal processing device and the control device process the electrical signal captured by the image sensor to display an image on a display device connected thereto, and output a driving signal for driving and controlling gain adjustment of the image sensor and the like.

The operating unit 3 includes a bending knob 12 for bending the bending part 6 in the up and down and the right and left directions, a treatment tool insertion part 13 for inserting a treatment tool such as a biopsy forceps and a laser probe into a body cavity, and a plurality of switches 14 for operating the signal processing device, the control device, and peripheral devices such as an air-supplying, a water-supplying, and a gas-supplying means. The endoscope apparatus 1 in which a treatment tool is inserted into a treatment tool insertion slot causes a distal end treatment part of the treatment tool to protrude through an insertion channel provided inside, and performs a biopsy wherein a diseased tissue is collected by the biopsy forceps, for example.

Figure 2:
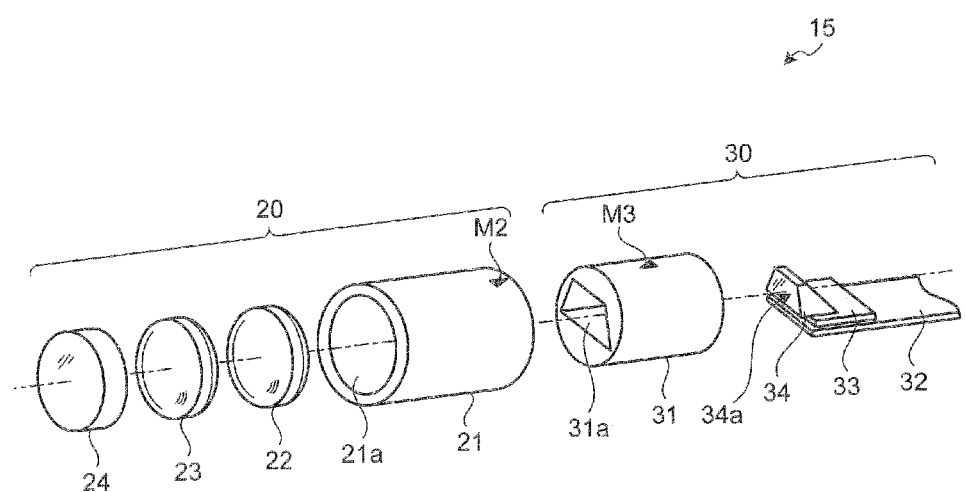
FIG. 2 is an exploded perspective view of an imaging module incorporated in a distal end of the endoscope apparatus shown in FIG. 1.
Figure 3:
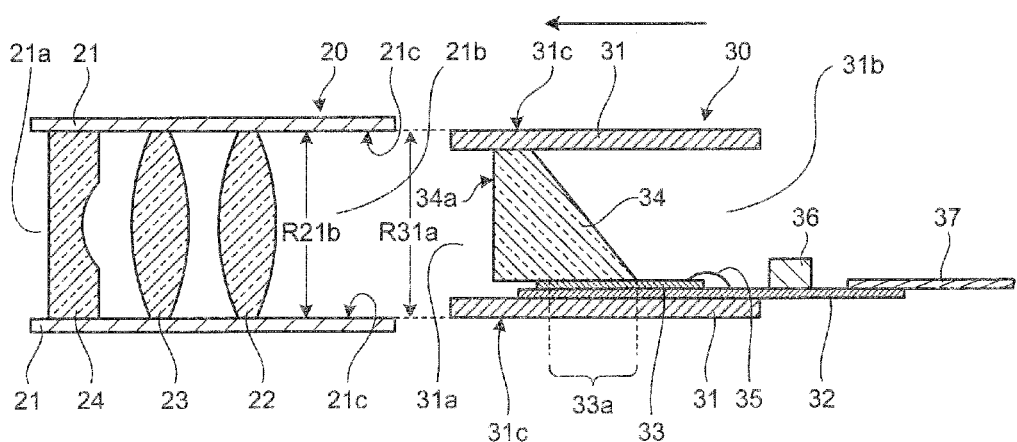
FIG. 3 is a cross-sectional view of the imaging module shown in FIG. 2.
Figure 3:
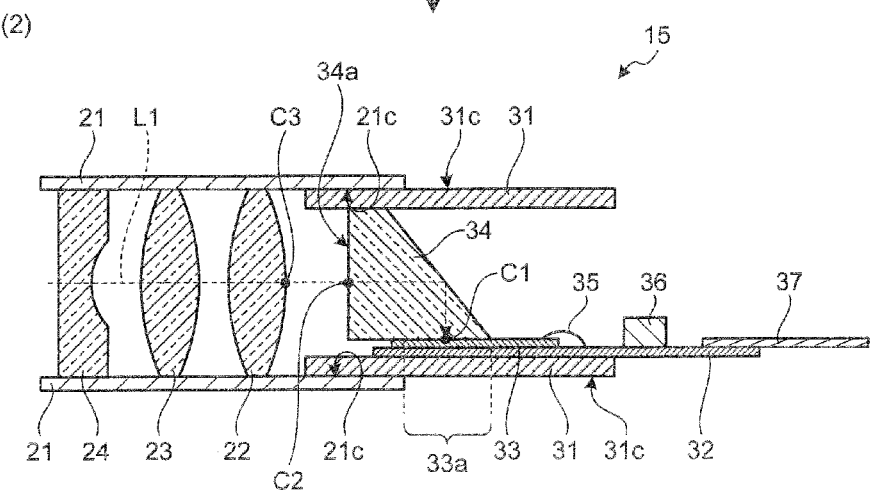

Next, a configuration of the imaging module incorporated in the distal end part 5 of the endoscope apparatus 1 will be described. FIG. 2 is an exploded perspective view of the imaging module incorporated in the distal end part 5 of the endoscope apparatus 1 shown in FIG. 1. FIG. 3 is a cross-sectional view of the imaging module shown in FIG. 2, and is the cross-sectional view obtained by cutting by a vertical surface with respect to a surface of a light-receiving region of the image sensor that constitutes the imaging module.

As shown in FIGS. 2 and 3, an imaging module 15 incorporated in the distal end part 5 of the endoscope apparatus 1 shown in FIG. 1 includes a lens unit 20 having a plurality of objective lenses, and an imaging unit 30 having an image sensor 33.

The lens unit 20 includes a hollow cylindrical lens holder 21 formed of light shielding material and open at both ends, lenses 22 and 23 that collect light from outside, and an observation window 24 that transmits the light from outside.

The size of the opening of the lens holder 21 coincides with outer circumferences of the lenses 22 and 23 and the observation window 24, and as shown in FIGS. 3(1) and 3(2), the lenses 22 and 23 and the observation window 24 are assembled in the lens holder 21 such that each center thereof is positioned on the same axis. At assembling each optical member of the lens holder 21, the shapes of each optical member and the lens holder 21 are designed such that an outer diameter central axis of the lens holder 21 and centers of the lenses 22 and 23 and the observation window 24, that is, an optical axis center of the lens unit 20 including the lenses 22 and 23 and the observation window 24 are aligned with each other. Note that the lens holder 21 is formed of corrosion-resistant steel, for example, and at least the outside thereof is shielded.

The light from outside input to the lens holder 21 from an opening part 21a at an end portion of the lens holder 21 through the observation window 24 is collected by the lenses 22 and 23. Then, the light collected by the lenses 22 and 23 is output from an opening part 21b at the other end of the lens holder 21. Any part in a circumferential direction of an output-side end portion at the opening part 21b side of the lens holder 21 has almost uniform thickness.

The imaging unit 30 includes a hollow columnar imaging holder 31 open at both ends, the image sensor 33 mounted on a substrate 32, and a prism 34 placed on the image sensor 33. The imaging holder 31 is, for example, formed of corrosion-resistant steel.

The image sensor 33 is a bare-chip type semiconductor device exemplified by a CCD or a CMOS image sensor, and has an imaging function that receives the light from the object and captures an image of the object. As shown in FIG. 3, a light-receiving region 33a that receives the light from the object and performs the photoelectric conversion processing of the received light is formed on an upper surface of a chip substrate of the image sensor 33. The image sensor 33 is arranged such that an optical axis of the lens unit 20 and a surface of the light-receiving region 33a are approximately parallel to each other when the imaging module 15 is assembled.

The light-receiving region 33a is realized by using a group of pixels arranged in a predetermined shape such as a lattice shape, a microlens formed on the group of pixels for efficiently collecting the light, and the like. The surface of the light-receiving region 33a has a rectangular shape, and the light-receiving region 33a is formed at a predetermined position on the chip substrate of the image sensor 33. Also, the image sensor 33 includes a driving circuit unit (not shown) in which a driving circuit for executing an imaging operation is formed and an electrode for external connection (not shown).

The image sensor 33 is mounted on the substrate 32 by connecting the electrode for external connection and the electrode for external connection on the substrate 32 by a wire 35. At this time, the image sensor 33 is mounted on the substrate 32 with a surface on which the light-receiving region 33a is formed as an upper surface. The light-receiving region 33a performs the photoelectric conversion processing of the received light, and the driving circuit unit generates an image signal of the object based on the signal subjected to the photoelectric conversion processing in the light-receiving region 33a, and outputs the generated image signal to the substrate 32 via the electrode for external connection. The image signal output to the substrate 32 is transferred to the signal processing device or the control device by a distribution cable 37 connected to the substrate 32. Note that parts 36 for signal control may be mounted on the substrate 32.

The prism 34 is placed on the light-receiving region 33a of the image sensor 33, and deflects the light from outside. The light deflected by the prism 34 is received by the light-receiving region 33a of the image sensor 33. A recess part (not shown) for forming an air gap is formed right above a microlens of the light-receiving region 33a at a base of the prism 34. The prism 34 has a square columnar shape with a trapezoid light-input surface 34a. Further, as shown in FIG. 3(2), the prism 34 is mounted on the image sensor 33 such that the light having passed through a position shown as a point C2 of the light-input surface 34a of the prism 34 is deflected on a deflecting surface of the prism 34, and then reaches the center C1 of the light-receiving region 33a of the image sensor 33. The point C2 corresponds to the center of a reference region, which is a region of the light-input surface 34a of the prism 34, and into which the light to be received by the light-receiving region 33a is input.

The imaging holder 31 has a hollow shape obtained by hollowing out a column with a square column having a trapezoid base. Further, the sizes of opening parts 31a and 31b are set such that the substrate 32, the image sensor 33, and the prism 34 can be assembled in the imaging holder 31 through the opening part 31b under the condition that each of the substrate 32, the image sensor 33, and the prism 34 has been mounted. For example, the sizes of the opening parts 31a and 31b in a height direction almost coincide with the sum of the substrate thickness of the substrate 32, the substrate thickness of the image sensor 33, and the height of the light-input surface of the prism 34, and the sizes of the opening parts 31a and 31b in a width direction are larger than the size of the substrate 32 in a narrow side direction. The substrate 32, the image sensor 33, and the prism 34 are assembled in the imaging holder 31 under the condition that each of them has been mounted.

At this time, the substrate 32, the image sensor 33, and the prism 34 are assembled in the imaging holder 31 by fixing a part of an outer circumferential surface of the light-input surface 34a of the prism 34 into an inner circumferential surface of the imaging holder 31. Note that the shapes of each optical member and the imaging holder 31 may be designed such that the point C2, which is the center of the reference region of the light-input surface 34a of the prism 34, is positioned on an outer diameter central axis of the imaging holder 31 when each optical member of the imaging holder 31 is assembled.

Here, an inner diameter of a light-output-side end portion of the lens holder 21 and an outer diameter of a light-input-side end portion of the imaging holder 31 are set to coincide with each other. That is, an inner diameter R21b of the opening part 21b of the lens holder 21 and an outer diameter R31a of the opening part 31a of the imaging holder 31 have the same diameter.

Therefore, the light-output-side end portion of the lens holder 21 and the light-input-side end portion of the imaging holder 31 can be directly fitted to each other as shown in FIG. 3(2) by inserting the light-input-side end portion of the imaging holder 31 into the lens holder 21 through the opening part 21b of the lens holder 21 as shown by the arrow in FIG. 3(1).

As described above, an outer diameter central axis of the lens holder 21 and the optical axis center of the lens unit 20 are aligned with each other, and the point C2, which is the center of the reference region of the light-input surface 34a of the prism 34, is positioned on the outer diameter central axis of the imaging holder 31. Therefore, the optical axis center of the lens unit 20 that passes through the center C3 of the lens 22, and the point C2, which is the center of the reference region of the light-input surface 34a of the prism 34, become positioned on the same axis L1 when the imaging holder 31 is inserted into the lens holder 21.

As described above, the lens holder 21 and the imaging holder 31 are designed such that the optical axis centers of the lenses 22 and 23 assembled to the lens holder 21 passes through the point C2, which is the center of the reference region of the prism 34 fixed in the imaging holder 31, based on the sizes of each configuration member of the lens unit 20 and the imaging holder 31, the optical axis of each optical system, and the like when the light-output-side end portion of the lens holder 21 and the light-input-side end portion of the imaging holder 31 are fitted to each other. Further, a part of the outer circumferential surface of the light-input surface of the prism 34 is fixed in the inner circumferential surface of the imaging holder 31. Therefore, the position of an inner circumferential surface 21c of the light-output-side end portion of the lens holder 21 is defined by an outer circumferential surface 31c of the imaging holder 31 such that the optical axis center of the lens unit 20, and the point C2, which is the center of the reference region of the light-input surface 34a of the prism 34, are positioned on the same axis L1.

Further, the prism 34 is mounted on the image sensor such that the light having passed through the point C2, which is the center of the reference region of the light-input surface 34a of the prism 34, reaches the center C1 of the light-receiving region 33a. Therefore, the collected light by each of the lenses 22 and 23 of the lens holder 21 is input to the light-input surface 34a of the prism 34 under the condition that the optical axis center is aligned with the center of the light-receiving region 33a of the image sensor 33. Therefore, the optical axis center of the optical member including each of the lenses 22 and 23 of the lens unit 20 and the center of the light to be received by the light-receiving region 33a of the image sensor 33 of the imaging unit 30 become aligned with each other when the light-output-side end portion of the lens holder 21 and the light-input-side end portion of the imaging holder 31 are fitted to each other.

Further, as shown in FIG. 2, a triangular mark M2 is put on a collected-light-output-side end portion of an outer circumferential surface of the lens holder 21, and a triangular mark M3 is put on the light-input-side end portion of the outer circumferential surface 31c of the imaging holder 31. The marks M2 and M3 are put to define the positions of each holder in the direction of the axis L1 and in a circumferential direction (circumferential direction of the axis L1 as the center) of each holder.

At assembling, first, an adhesive is applied to at least one of the inner circumferential surface 21c of the output-side end portion of the lens holder 21 and the outer circumferential surface 31c of the input-side end portion of the imaging holder 31. Next, the imaging holder 31 is fitted into the lens holder 21 such that an apex of the mark M2 of the lens holder 21 and an apex of the mark M3 of the imaging holder 31 are positioned on the same axis as viewed from above. Then, the imaging holder 31 is inserted into the lens holder 21 until the apex of the mark M3 of the imaging holder 31 reaches the apex of the mark M2 of the lens holder 21. Note that adhesive hardening processing is further performed depending on the type of the adhesive.

As described above, in the imaging module 15 according to the first embodiment, the position of the collected-light-output-side end portion of the lens holder 21 is defined by the outer circumferential surface of the imaging holder 31 such that the optical axis center of each optical member that passes through the center C3 of the lens 22, and the point C2, which is the center of the light-input surface 34a of the prism 34, are aligned with each other. In other words, in the imaging module 15, the position of the collected-light-output-side end portion of the lens holder 21 is defined by the outer circumferential surface of the imaging holder 31 such that the optical axis center of each optical member that passes through the center C3 of the lens 22 and the center of the light to be received by the light-receiving region 33a of the image sensor 33 are aligned with each other. Accordingly, the imaging module, in which the optical axis center of the optical member of the lens unit 20 and the center of the light to be received by the light-receiving region 33a of the imaging unit 30 of the image sensor 33 are aligned with each other, can be manufactured by the simple manufacturing process in such a way that the collected-light-output-side end portion of the lens holder 21 and the collected-light-input-side end portion of the imaging holder 31 are merely fitted to each other.

Further, in the imaging module 15, the positions of each holder in the direction of the axis L1 and in the circumferential direction of the axis L1 as the center can be accurately defined by simply fitting the collected-light-output-side end portion of the lens holder 21 and the collected-light-input-side end portion of the imaging holder 31 to each other such that the mark M2 put on the outer circumference of the lens holder 21 and the mark M3 put on the outer circumference of the imaging holder 31 meet each other.

Further, in the imaging module 15, since the collected-light-output-side end portion of the lens holder 21 and the collected-light-input-side end portion of the imaging holder 31 can be directly fitted to each other without other member, the distal end diameter of the insertion tool of the endoscope apparatus can be thinned and a loss of a light amount due to an intervening member can be reduced, whereby an excellent image can be obtained.

(Second Embodiment)

Next, a second embodiment will be described. In the second embodiment, an imaging module assembled by inserting a lens holder into an imaging holder will be described.

Figure 4:
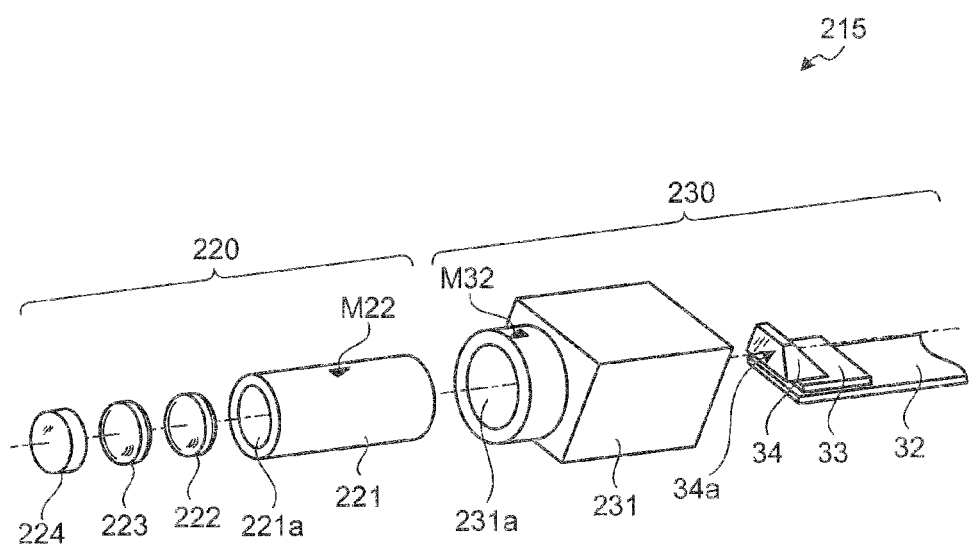
FIG. 4 is an exploded perspective view of an imaging module according to a second embodiment.
Figure 5:
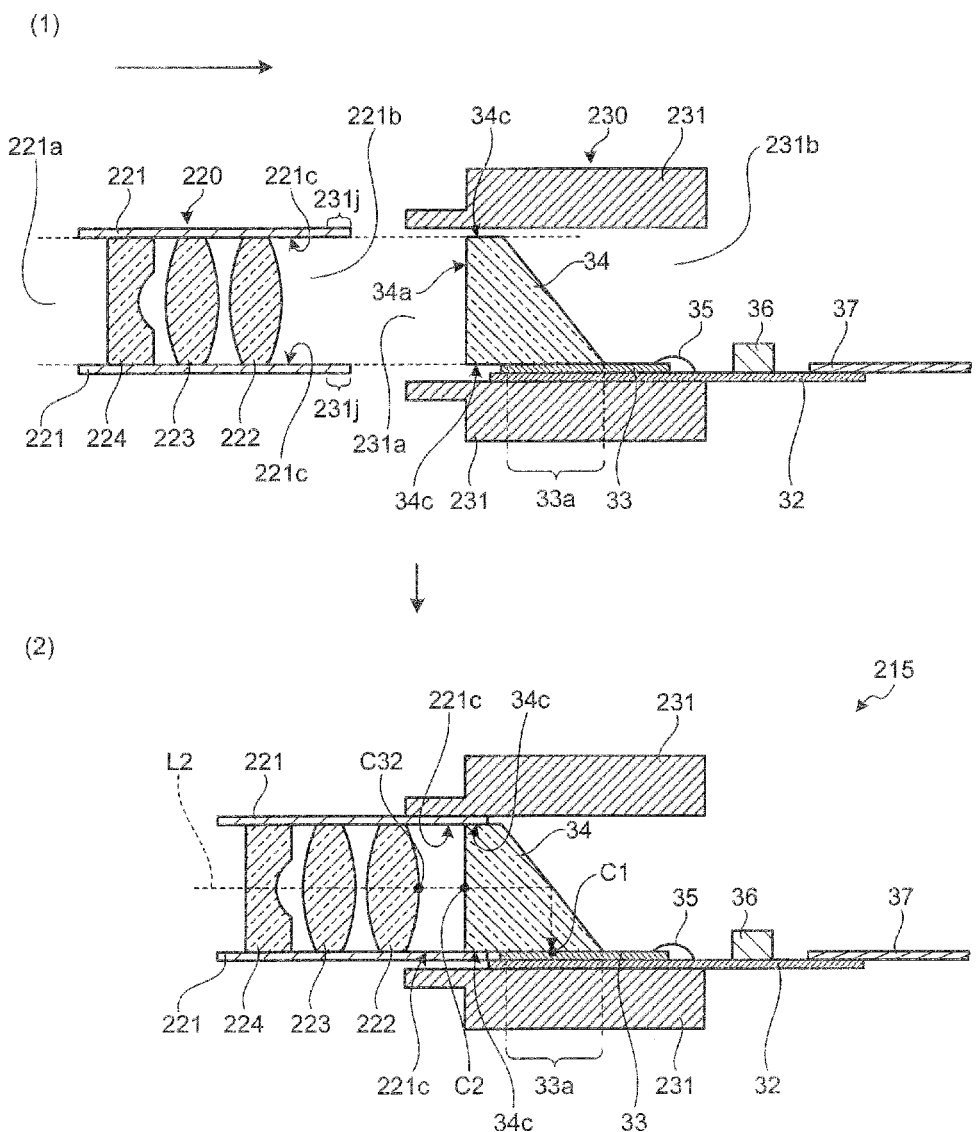
FIG. 5 is a cross-sectional view of the imaging module shown in FIG. 4.

FIG. 4 is an exploded perspective view of an imaging module according to the second embodiment, and FIG. 5 is a cross-sectional view of the imaging module shown in FIG. 4, and is the cross-sectional view obtained by cutting by a vertical surface with respect to a surface of a light-receiving region of an image sensor that constitutes the imaging module. As shown in FIGS. 4 and 5, an imaging module 215 according to the second embodiment includes a lens unit 220 and an imaging unit 230 having an image sensor 33.

The lens unit 220 includes a hollow columnar lens holder 221 open at both ends, lenses 222 and 223 that collect light from outside, and an observation window 224 through which the light from outside is transmitted.

An opening part 221a of the lens holder 221 has a circular shape, the size of which coincides with outer circumferences of the lenses 222 and 223 and the observation window 224. As shown in FIGS. 5(1) and 5(2), the lenses 222 and 223 and the observation window 224 are assembled in the lens holder 221 such that each center thereof is positioned on the same axis as an outer diameter central axis of the lens holder 221. The light from outside input into the lens holder 221 from the opening part 221a at an end portion of the lens holder 221 through the observation window 224 is collected by the lenses 222 and 223, and the collected light is output from an opening part 221b at the other end of the lens holder 221. At least a portion (end portion 231j shown in FIG. 5(1)) of the opening part 221b of the lens holder 221, which is in contact with an outer circumferential surface of a prism 34, has a trapezoid opening shape that is the same as a light-input surface 34a of the prism 34. Note that the lens holder 221 is, for example, formed of corrosion-resistant steel, and at least the outside thereof is shielded.

The imaging unit 230 includes a hollow imaging holder 231 open at both ends, the image sensor 33 mounted on a substrate 32, and the prism 34 placed on the image sensor 33. The imaging holder 231 is, for example, formed of corrosion-resistant steel.

The imaging holder 231 has a shape such that a column is protruded from one side surface of a square column. A column portion of the imaging holder 231 has an approximately hollow cylindrical shape, and a square column portion has a hollow shape obtained by hollowing out the square column having a trapezoid base.

The size of an opening part 231b of the square column portion of the imaging holder 231 is set such that the substrate 32, the image sensor 33, and the prism 34 can be assembled through the opening part 231b in the imaging holder 231 under the condition that each of the substrate 32, the image sensor 33, and the prism 34 has been mounted. The substrate 32, the image sensor 33, and the prism 34 are assembled in the imaging holder 231 by fixing a part of a base of the substrate 32 to an inner circumferential surface of the imaging holder 231. For example, the shapes of each optical member and the imaging holder 231 are designed such that a point C2, which is the center of a reference region of the light-input surface 34a of the prism 34, is positioned on an outer diameter central axis of the imaging holder 231 at assembling each optical member of the imaging holder 231. Note that, similar to the first embodiment, the prism 34 is mounted on the image sensor 33 such that the light having passed through the point C2 of the light-input surface 34a of the prism 34 reaches the center C1 of a light-receiving region 33a of the image sensor 33, as shown in FIG. 5(2).

Further, an inner diameter of a circular opening part 231a of the column portion of the imaging holder 231 to which the collected light output from the lens unit 220 is input is larger than an outer diameter of the lens holder 221. Therefore, a light-output-side end portion of the lens holder 221 and a light-input-side end portion of the imaging holder 231 can be directly fitted to each other as shown in FIG. 5(2) by fitting the light-output-side end portion of the lens holder 221 into the imaging holder 231 through the opening part 231a of the column portion of the imaging holder 231, as shown by the arrow in FIG. 5(1).

Here, the shapes of the lens holder 221 and the imaging holder 231 are designed such that an optical axis center of the lens unit 220 that passes through the center C32 of the lens 222 passes through the point C2 of the light-input surface 34a of the prism 34 fixed in the imaging holder 231 when the light-output-side end portion of the lens holder 221 and the light-input-side end portion of the imaging holder 231 are fitted to each other. Further, the shape of the opening of the end portion 231j of the opening part 221b of the lens holder 221 and the shape of the light-input surface 34a of the prism 34 assembled to the imaging holder 231 are formed to have the same shape, and the position of the lens holder 221 in the up and down and the right and left directions in FIG. 5(2) is defined by directly fitting an inner circumferential surface 221c of the lens holder 221 onto an outer circumferential surface 34c of the prism 34. That is, the position of the inner circumferential surface 221c of the light-output-side end portion of the lens holder 221 is directly defined by the outer circumferential surface 34c of the prism 34 such that the optical axis center of the lens unit 220 that passes through the center C32 of the lens 222 and the point C2 of the light-input surface 34a of the prism 34 are positioned on the same axis L2 when the light-output-side end portion of the lens holder 221 and the light-input-side end portion of the imaging holder 231 are fitted to each other. The prism 34 is mounted on the image sensor 33 such that the light having passed through the point C2 of the light-input surface 34a reaches the center C1 of the light-receiving region 33a. Therefore, the optical axis center of the optical member of the lens unit 220 and the center of the light to be received by the light-receiving region 33a of the image sensor 33 of the imaging unit 230 become aligned with each other. Note that a part of an outer circumferential surface of the light-output-side end portion of the lens holder 221 is also defined by a part of an inner circumferential surface of the imaging holder 231.

Further, similar to the first embodiment, a triangular mark M22 and a triangular mark M32 for defining the positions of each holder in the direction of the axis L2 and in the circumferential direction of each holder (circumferential direction of the axis L2 as the center) are respectively put on the outer circumferential surface of the collected-light-output-side end portion of the lens holder 221 and an outer circumferential surface of the light-input-side end portion of the imaging holder 231, as shown in FIG. 4.

At assembling, first, an adhesive is applied to the inner circumferential surface 221c of the output-side end portion of the lens holder 221. Next, the lens holder 221 is fitted into the imaging holder 231 such that an apex of the mark M22 of the lens holder 221 and an apex of the mark M32 of the imaging holder 231 are positioned on the same axis as viewed from above. Further, the lens holder 221 is inserted into the imaging holder 231 until the apex of the mark M22 of the lens holder 221 reaches the apex of the mark M32 of the imaging holder 231. Note that adhesive hardening processing is further performed depending on the type of the adhesive.

As described above, the optical axis center of the optical member of the lens unit 220 and the center of the light to be received by the light-receiving region 33a of the image sensor 33 of the imaging unit 230 are aligned with each other, and further, the positions of each holder in the direction of the axis L2 and in the circumferential direction of the axis L2 as the center can be accurately defined by simply fitting the collected-light-output-side end portion of the lens holder 221 and the collected-light-input-side end portion of the imaging holder 231 to each other such that the mark M22 and the mark M32 meet to each other when the position of the light-output-side end portion of the lens holder 221 is defined by the outer circumferential surface 34c of the prism 34.

(Third Embodiment)

Next, a third embodiment will be described. In the third embodiment, a case will be described wherein the position of a collected-light-output-side end portion of a lens holder is defined by a columnar protrusion portion formed on a light-input surface of a prism.

Figure 6:
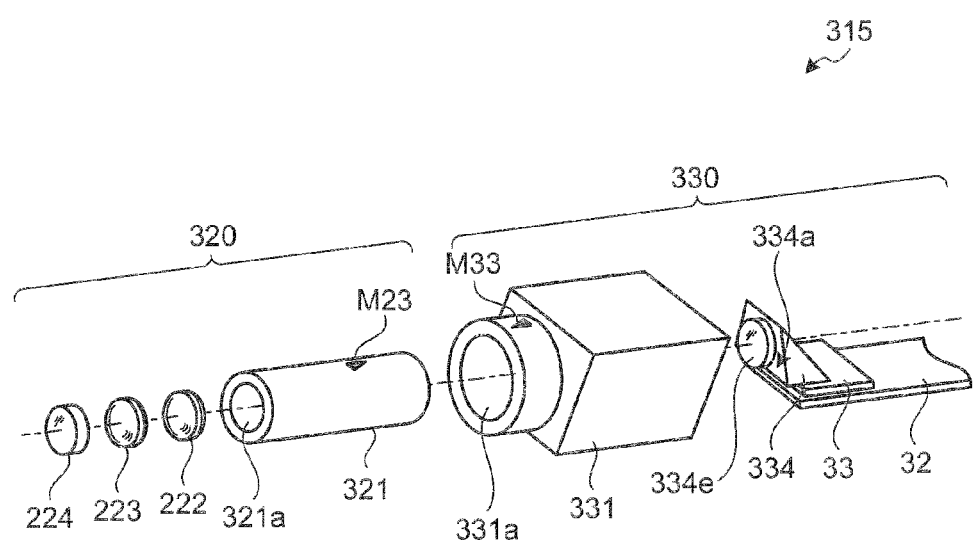
FIG. 6 is an exploded perspective view of an imaging module according to a third embodiment.
Figure 7:
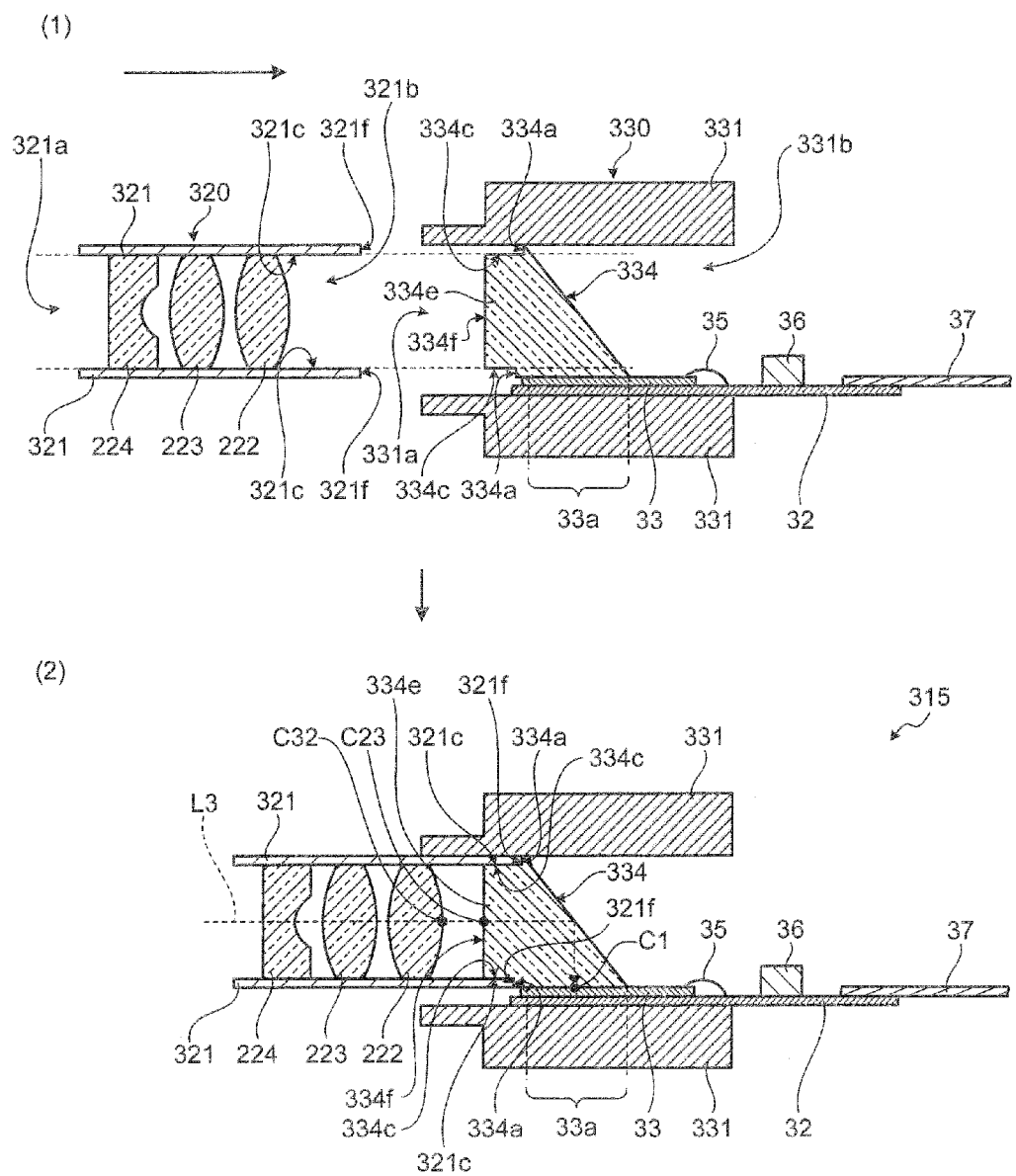
FIG. 7 is a cross-sectional view of the imaging module shown in FIG. 6.

FIG. 6 is an exploded perspective view of an imaging module according to the third embodiment, and FIG. 7 is a cross-sectional view of the imaging module shown in FIG. 6, and is the cross-sectional view obtained by cutting by a vertical surface with respect to a surface of a light-receiving region of an image sensor that constitutes the imaging module. As shown in FIGS. 6 and 7, an imaging module 315 according to the third embodiment includes a lens unit 320 and an imaging unit 330 having an image sensor 33.

The lens unit 320 includes a hollow cylindrical lens holder 321 open at both ends, lenses 222 and 223 that collect light from outside, and an observation window 224 through which the light from outside is transmitted. The size of the opening of the lens holder 321 coincides with outer circumferences of the lenses 222 and 223 and the observation window 224, and as shown in FIGS. 7(1) and 7(2), the lenses 222 and 223 and the observation window 224 are assembled in the lens holder 321 such that each center thereof is positioned on the same axis as an outer diameter central axis of the lens holder 321. The light from outside input to the lens holder 321 from an opening part 321a at an end portion of the lens holder 321 through the observation window 224 is collected by the lenses 222 and 223, and the collected light is output from an opening part 321b at the other end of the lens holder 321. Note that the lens holder 321 is, for example, formed of corrosion-resistant steel, and at least the outside thereof is shielded.

The imaging unit 330 includes a hollow imaging holder 331 open at both ends, the image sensor 33 mounted on a substrate 32, and a prism 334 placed on the image sensor 33. The imaging holder 331 is, for example, formed of corrosion-resistant steel.

A prism 334 has a shape such that a columnar protrusion portion 334e is formed on a light-input surface 334a that is one side surface of a triangle pole. The outer diameter of the protrusion portion 334e is set to coincide with the inner diameter of a collected-light-output-side end portion at the opening part 321b side of the lens holder 321.

The imaging holder 331 has a shape such that a column is protruded from one side surface of a square column similar to the imaging holder 231. The column portion has an approximately hollow cylindrical shape, and the square column portion has a hollow shape obtained by hollowing out the square column having a trapezoid base.

The size of an opening part 331b of the square column portion of the imaging holder 331 is set such that the substrate 32, the image sensor 33, and the prism 334 can be assembled in the imaging holder 331 through the opening part 331b under the condition that each of them has been mounted. The substrate 32, the image sensor 33, and the prism 334 are assembled in the imaging holder 331 by fixing a part of a base of the substrate 32 into an inner circumferential surface of the imaging holder 331. For example, the shapes of each optical member and the imaging holder 331 are designed such that a point C23 of the prism 334 is positioned on an outer diameter central axis of the imaging holder 331 at assembling each optical member of the imaging holder 331. The point C23 corresponds to the center of a reference region, which is a region of a surface 334f of the protrusion portion 334e of the light-input surface 334a, and into which the light to be received by a light-receiving region 33a of the image sensor 33 is input. Note that the prism 334 is, similar to the first embodiment, mounted on the image sensor 33 such that the light having passed through the point C23 of the prism 334 reaches the center C1 of the light-receiving region 33a of the image sensor 33, as shown in FIG. 7(2).

Further, the inner diameter of a circular opening part 331a of the column portion of the imaging holder 331 into which the collected light output from the lens unit 320 is input is larger than the outer diameter of the lens holder 321. Therefore, the light-output-side end portion of the lens holder 321 and a light-input-side end portion of the imaging holder 331 can be directly fitted to each other as shown in FIG. 7(2) by fitting the light-output-side end portion of the lens holder 321 into the imaging holder 331 through the opening part 331a of the column portion of the imaging holder 331 as shown by the arrow in FIG. 7(1).

Here, the lens holder 321 and the imaging holder 331 are designed such that an optical axis center of the lens unit 320 that passes through the center C32 of the lens 222 passes through the point C23 of the prism 334 fixed in the imaging holder 331 when the light-output-side end portion of the lens holder 321 and the light-input-side end portion of the imaging holder 331 are fitted to each other. Further, the inner diameter of the opening part 321b of the lens holder 321 and the outer diameter of the protrusion portion 334e of the light-input surface 334a of the prism 334 are formed to coincide with each other, and the position of the lens holder 321 in the up and down direction in FIG. 7(2) is defined by directly fitting an inner circumferential surface 321c of the lens holder 321 onto an outer circumferential surface 334c of the protrusion portion 334e of the prism 334. The position of the inner circumferential surface 321c of the light-output-side end portion of the lens holder 321 is directly defined by the outer circumferential surface 334c of the protrusion portion 334e of the prism 334 such that the optical axis center of the lens unit 320 that passes through the center C32 of the lens 222 and the point C23 of the prism 334 are positioned on the same axis as an axis L3 when the light-output-side end portion of the lens holder 321 and the light-input-side end portion of the imaging holder 331 are fitted to each other. Further, the prism 334 is mounted on the image sensor 33 such that the light having passed through the point C23 reaches the center C1 of the light-receiving region 33a. Therefore, the optical axis center of the optical member of the lens unit 320 and the center of the light to be received by the light-receiving region 33a of the image sensor 33 of the imaging unit 330 become aligned with each other when the light-output-side end portion of the lens holder 321 and the light-input-side end portion of the imaging holder 331 are fitted to each other. Note that the position of a part of an outer circumferential surface of the light-output-side end portion of the lens holder 321 is also defined by a part of an inner circumferential surface of the imaging holder 331.

Further, the position of a collected-light-output-side end portion of the lens holder 321 in the direction of the axis L3 is defined by causing a distal end 321f to meet the light-input surface 334a of the prism 334. Further, similar to the first embodiment, a triangular mark M23 and a triangular mark M33 for defining the positions of each holder in the direction of the axis L3 and in the circumferential direction of each holder (circumferential direction of the axis L3 as the center) are respectively put on the outer circumferential surface of the collected-light-output-side end portion of the lens holder 321, and an outer circumferential surface of the light-input-side end portion of the imaging holder 331, as shown in FIG. 6.

At assembling, first, an adhesive is applied to the inner circumferential surface 321c of the output-side end portion of the lens holder 321. Next, the lens holder 321 is fitted into the imaging holder 331 such that an apex of the mark M23 of the lens holder 321 and an apex of the mark M33 of the imaging holder 331 are positioned on the same axis as viewed from above. Further, the lens holder 321 is inserted into the imaging holder 331 until the distal end 321f of the collected-light-output-side end portion of the lens holder 321 meets the light-input surface 334a of the prism 334. Note that adhesive hardening processing is further performed depending on the type of the adhesive.

As described above, the optical axis center of the optical member of the lens unit 320 and the center of the light to be received by the light-receiving region 33a of the image sensor 33 of the imaging unit 330 can be aligned with each other, and further, the positions of each holder in the direction of the axis L3 and in the circumferential direction of the axis L3 as the center can be easily and accurately defined by simply fitting the collected-light-output-side end portion of the lens holder 321 and the collected-light-input-side end portion of the imaging holder 331 to each other such that the mark M23 and the mark M33 meet to each other, and by inserting the lens holder 321 into the imaging holder 331 until the distal end 321f of the collected-light-output-side end portion of the lens holder 321 meets the light-input surface 334a of the prism 334 when the position of the light-output-side end portion of the lens holder 321 is defined by the outer circumferential surface 334c of the protrusion portion 334e of the prism 334.

(Modification of Third Embodiment)

Next, Modification of the third embodiment will be described. In Modification of the third embodiment, a case will be described wherein the position of a collected-light-output-side end portion of a lens holder is defined by a frame-shaped protrusion portion formed on a light-input surface of a prism.

Figure 8:
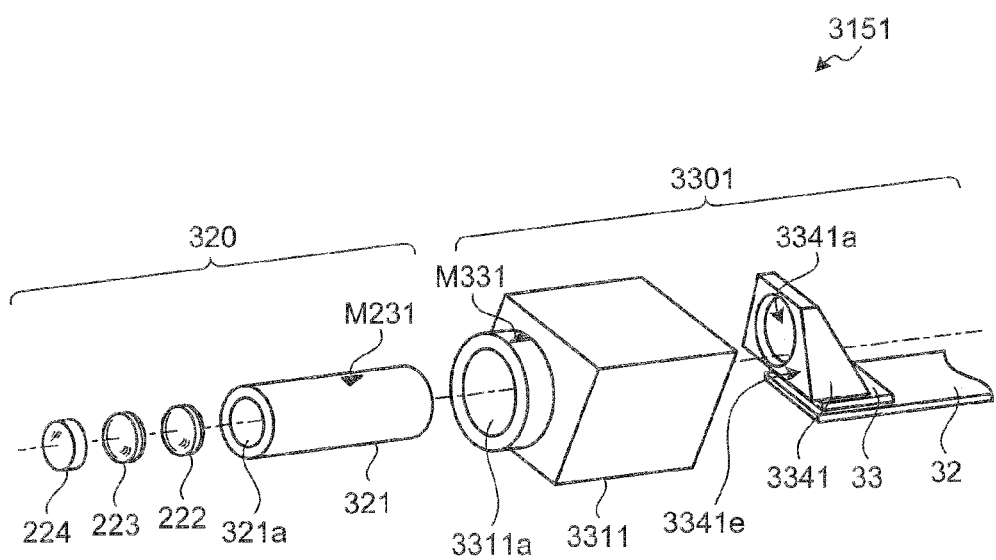
FIG. 8 is an exploded perspective view of an imaging module according to Modification of the third embodiment.
Figure 9:
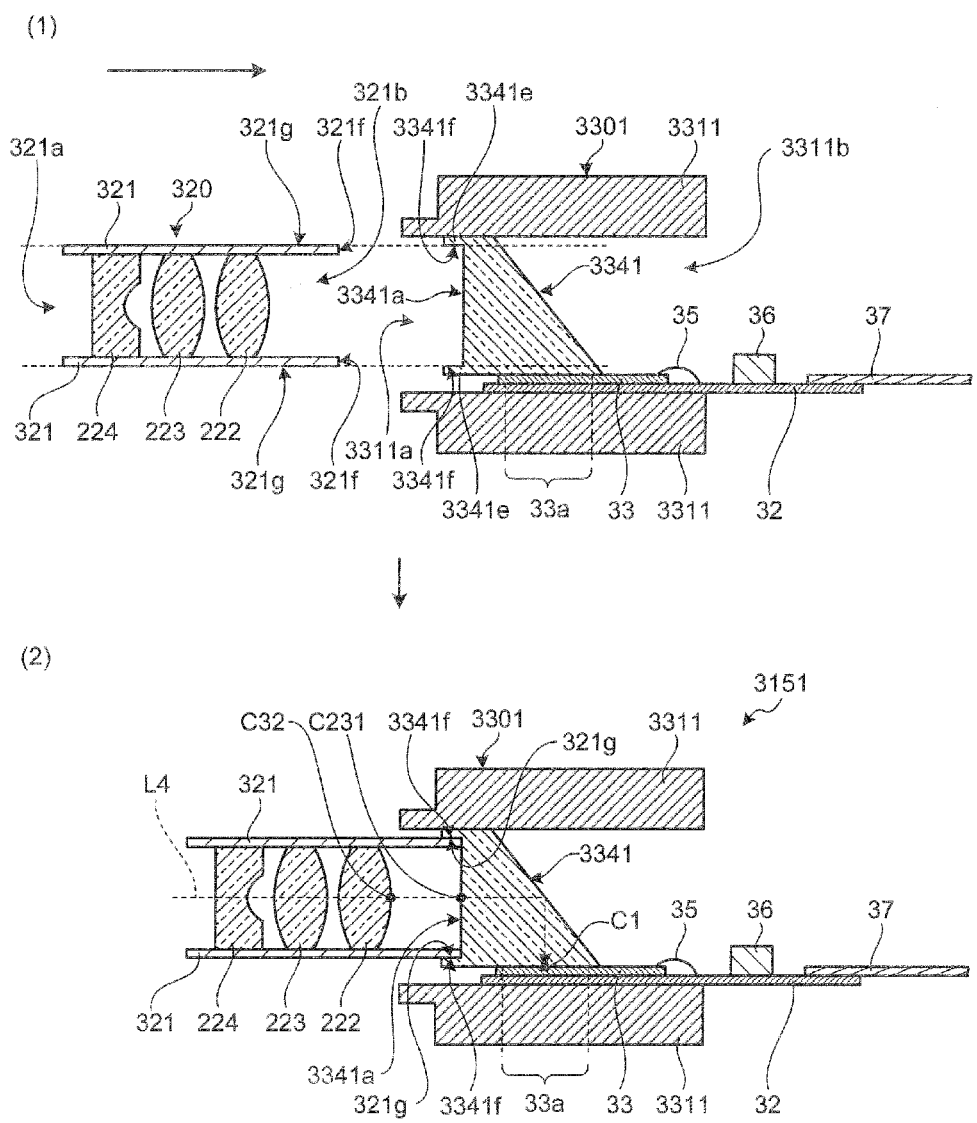
FIG. 9 is a cross-sectional view of the imaging module shown in FIG. 8.

FIG. 8 is an exploded perspective view of an imaging module according to Modification of the third embodiment, and FIG. 9 is a cross-sectional view of the imaging module shown in FIG. 8, and is the cross-sectional view obtained by cutting by a vertical surface with respect to a surface of a light-receiving region of an image sensor that constitutes the imaging module. An imaging module 3151 according to the third embodiment, as shown in FIGS. 8 and 9, includes a lens unit 320 and an imaging unit 3301 having an image sensor 33.

An imaging unit 3301 includes a hollow imaging holder 3311 open at both ends, an image sensor 33 mounted on a substrate 32, and a prism 3341 placed on the image sensor 33. The imaging holder 3311 is, for example, formed of corrosion-resistant steel.

The prism 3341 has a square columnar shape having a trapezoid light-input surface 3341a, and a frame-shaped protrusion portion 3341e having the inner diameter that coincides with the outer diameter of a collected-light-output-side end portion at an opening part 321b side of a lens holder 321, and formed on the light-input surface 3341a. The prism 3341 can be seen such that a circular opening is formed on the light-input surface of the prism 3341, the opening having a diameter that coincides with the outer diameter of the collected-light-output-side end portion at the opening part 321b side of the lens holder 321, when seen from a collected-light-input direction side.

The imaging holder 3311 has a shape such that a column protrudes from one side surface of a square column, similar to the imaging holder 231. The column portion has an approximately hollow cylindrical shape, and the square column portion has a hollow shape obtained by hollowing out the square column having a trapezoid base.

The size of an opening part 3311b of the square column portion of the imaging holder 3311 is set such that a substrate 32, the image sensor 33, and the prism 3341 can be assembled in the imaging holder 3311 through the opening part 3311b under the condition that each of them has been mounted. The substrate 32, the image sensor 33, and the prism 3341 are assembled in the imaging holder 3311 by fixing a part of a base of the substrate 32 and a part of an outer circumferential surface of the light-input surface 3341a of the prism 3341 into an inner circumferential surface of the imaging holder 3311. For example, the shapes of each optical member and the imaging holder 3311 are designed such that a point C231 of the light-input surface 3341a of the prism 3341 is positioned on an outer diameter central axis of the imaging holder 3311 at assembling each optical member of the imaging holder 3311. The point C231 corresponds to the center of a reference region, that is a region of the light-input surface 3341a, and into which the light to be received by a light-receiving region 33a of the image sensor 33 is input. Note that, similar to the first embodiment, the prism 3341 is mounted on the image sensor 33 such that the light having passed through the center C231 of the light-input surface 3341a of the prism 3341 reaches the center C1 of the light-receiving region 33a of the image sensor 33, as shown in FIG. 9(2).

Further, the inner diameter of an opening part 3311a of the column portion of the imaging holder 3311 into which the collected light output from the lens unit 320 is input is larger than the outer diameter of the lens holder 321. Therefore, a light-output-side end portion of the lens holder 321 and a light-input-side end portion of the imaging holder 3311 can be directly fitted to each other as shown in FIG. 9(2) by simply fitting the light-output-side end portion of the lens holder 321 into the imaging holder 3311 through the opening part 3311a of the column portion of the imaging holder 3311 as shown by the arrow in FIG. 9(1).

The shapes of the lens holder 321 and the imaging holder 3311 are designed such that an optical axis center of the lens unit 320 that passes through the center C32 of the lens 222 passes through the point C231 of the prism 3341 fixed in the imaging holder 3311 when the light-output-side end portion of the lens holder 321 and the light-input-side end portion of the imaging holder 3311 are fitted to each other. Further, the outer diameter of the opening part 321b of the lens holder 321 and the inner diameter of a protrusion portion 3341e of the light-input surface 3341a of the prism 3341 are formed to coincide with each other. Therefore, the position of the lens holder 321 in the up and down direction in FIG. 9(2) can be defined by directly fitting an outer circumferential surface 321g of the lens holder 321 into an inner circumferential surface 3341f of the protrusion portion 3341e of the prism 3341. The position of the outer circumferential surface 321g of the light-output-side end portion of the lens holder 321 is directly defined by the inner circumferential surface 3341f of the protrusion portion 3341e of the prism 3341 such that the optical axis center of the lens unit 320 that passes through the center C32 of the lens 222 and the point C231 of the prism 3341 are positioned on the same axis L4 when the light-output-side end portion of the lens holder 321 and the light-input-side end portion of the imaging holder 3311 are fitted to each other. The prism 3341 is mounted on the image sensor 33 such that the light having passed through the point C231 reaches the center C1 of the light-receiving region 33a. Therefore, the optical axis center of the optical member of the lens unit 320 and the center of the light to be received by the light-receiving region 33a of the image sensor 33 of the imaging unit 3301 become aligned with each other when the light-output-side end portion of the lens holder 321 and the light-input-side end portion of the imaging holder 3311 are fitted to each other.

Further, the position of a collected-light-output-side end portion of the lens holder 321 in the direction of the axis L4 is defined by causing a distal end 321f to meet the light-input surface 3341a of the prism 3341. Note that, similar to the first embodiment, a triangular mark M231 and a triangular mark M331 for defining the position of each holder in the circumferential direction of the axis L4 as the center of each holder are respectively put on the outer circumferential surface of the collected-light-output-side end portion of the lens holder 321 and an outer circumferential surface of the light-input-side end portion of the imaging holder 3311, as shown in FIG. 8.

At assembling, first, an adhesive is applied to the outer circumferential surface 321g of the output-side end portion of the lens holder 321. Next, the lens holder 321 is fitted into the imaging holder 3311 such that an apex of the mark M231 of the lens holder 321 and an apex of the mark M331 of the imaging holder 3311 are positioned on the same axis as viewed from above. Then, the lens holder 321 is inserted into the imaging holder 3311 until the distal end 321f of the collected-light-output-side end portion of the lens holder 321 meets the light-input surface 3341a of the prism 3341. Note that adhesive hardening processing is further performed depending on the type of the adhesive.

As described above, the imaging module 3151 can be easily and accurately manufactured, similar to the imaging module 315, by simply inserting the lens holder 321 into the imaging holder 3311 until the distal end 321f of the collected-light-output-side end portion of the lens holder 321 meets the light-input surface 3341a of the prism 3341 when the position of the light-output-side end portion of the lens holder 321 is defined by the inner circumferential surface 3341f of the protrusion portion 3341e of the prism 3341.

Figure 10:
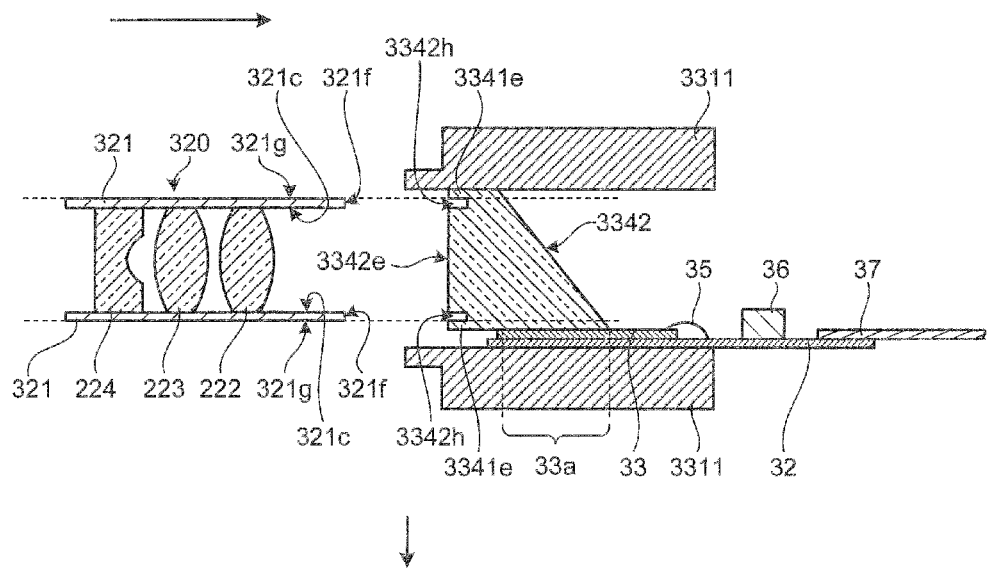
FIG. 10 is a cross-sectional view of another example of the imaging module according to Modification of the third embodiment.
Figure 10:
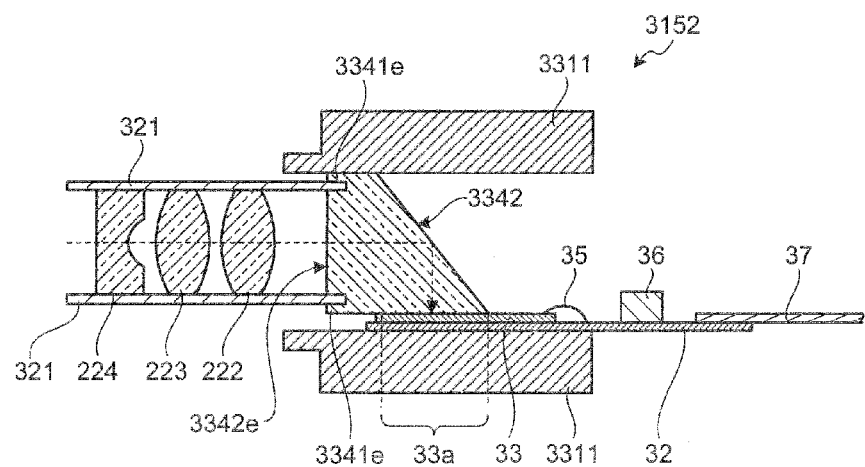

Note that, as shown by a prism 3342 of FIG. 10, a columnar protrusion portion 3342e having the outer diameter that coincides with the inner diameter of the collected-light-output-side end portion of the lens holder 321 at the opening part 321b side may be formed in a further inner circumference of the protrusion portion 3341e, so that the position of the outer circumferential surface 321g and the inner circumferential surface 321c of the light-output-side end portion of the lens holder 321 can be defined by the inner circumferential surface of the protrusion portion 3341e of the prism 3342 and the outer circumferential surface of the protrusion portion 3342e. In this case, an imaging module 3152 shown in FIG. 10(2) can be easily and accurately manufactured by simply fitting the light-output-side end portion of the lens holder 321 into the light-input-side end portion of the imaging holder 3311, and inserting the lens holder 321 into the imaging holder 3311 until the distal end 321f of the collected-light-output-side end portion of the lens holder 321 meets a ditch 3342h between the protrusion portion 3341e and the protrusion portion 3342e of the prism 3342 as shown by the arrow in FIG. 10(1).

Figure 11:
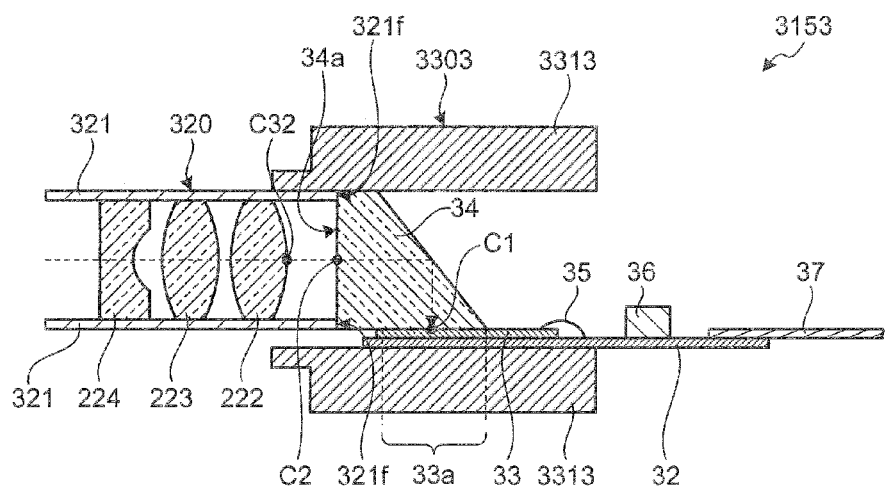
FIG. 11 is a cross-sectional view of another example of the imaging module according to Modification of the third embodiment.
Figure 12:
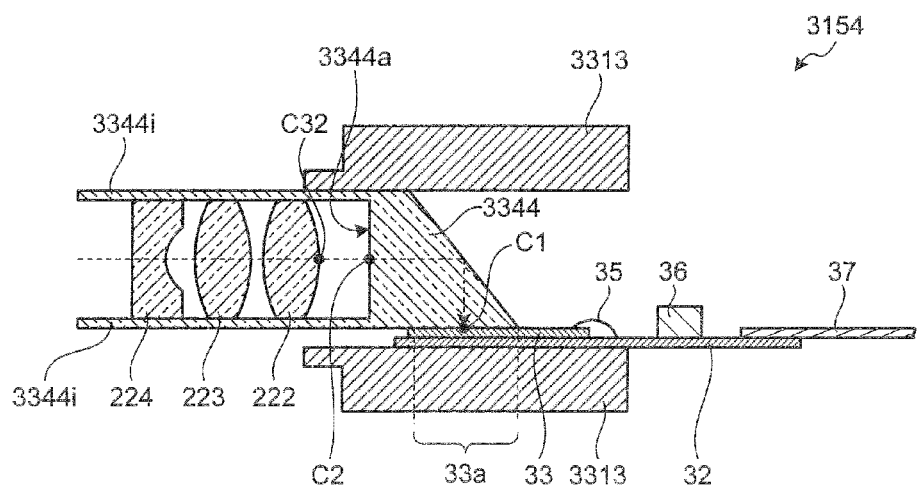
FIG. 12 is a cross-sectional view of another example of the imaging module according to Modification of the third embodiment.

Further, similar to an imaging module 3153 of FIG. 11, the imaging module may be further downsized by directly adhering the distal end 321f of the collected-light-output-side end portion of the lens holder 321 of the lens unit 320 to the light-input surface 34a of the prism 34 assembled to an imaging holder 3313 of an imaging unit 3303. Also, as shown by an imaging module 3154 of FIG. 12, a columnar hollow protrusion portion 3344i having the same shape as the lens holder 321 may be integrally formed with a light-input surface 3344a of a prism 3344, so that lenses 222 and 223 and an observation window 224 can be assembled in the protrusion portion 3344i.

Figure 13:
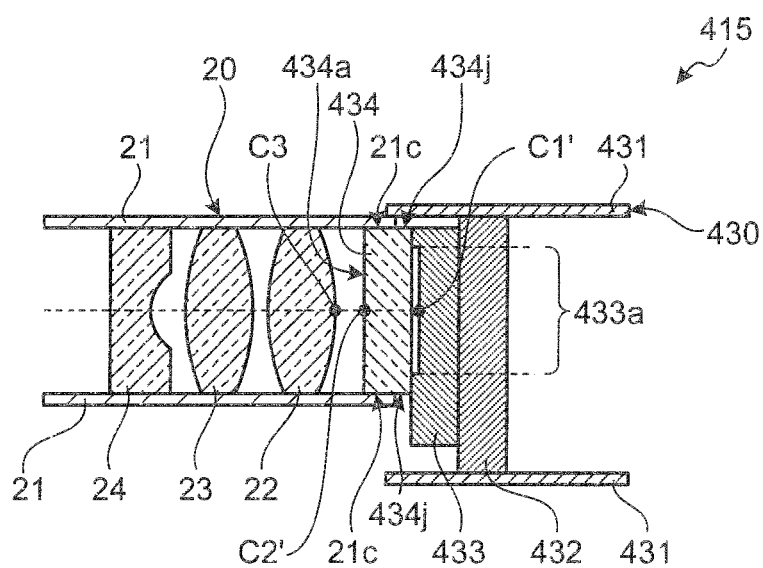
FIG. 13 is a cross-sectional view of another example of the imaging module according to Modification of the third embodiment.

Further, in the first to third embodiments, the prisms 34, 334, 3341, 3342, and 3344 have been exemplarily shown as the optical member placed in the image sensor 33, but not limited to these examples. For example, a plate-like glass 434 for transmitting collected light output from a lens holder 21 to an image sensor 433 can be used, similar to an imaging module 415 shown in FIG. 13.

In this case, a substrate 432 onto which the image sensor 433 is mounted is assembled in an imaging holder 431 of an imaging unit 430 such that an optical axis of the lens unit 20 and a light-receiving region 433a are perpendicular to each other at the completion of the imaging module 415. Further, the plate-like glass 434 is mounted on the image sensor 433 such that the center C2' of a light-input surface 434a of the plate-like glass 434 and the center C1' of the light-receiving region 433a of the image sensor 433 are positioned on the same axis. The center C2' corresponds to the center of a reference region into which the light to be received by the light-receiving region 433a is input, the reference region being a region of the light-input surface 434a of the plate-like glass 434. Further, the plate-like glass 434 has an approximately columnar shape, and the outer diameter of the plate-like glass 434 coincides with the inner diameter of the light-output-side end portion of the lens holder 21. Therefore, the position of the lens holder 21 is defined such that an optical axis center of the lens unit 20 that passes through the center C3 of the lens 22, the center C2' of the plate-like glass 434, and the center C1' of the light-receiving region 433a of the image sensor 433 are positioned on the same axis by fitting the inner circumferential surface of the lens holder 21 into an outer circumferential surface 434j of the plate-like glass 434.

Further, in the first to third embodiments, the imaging modules incorporated in the distal end of the insertion tool of the endoscope apparatus have been exemplarily described. However, of course, the imaging modules can be applied to various types of electronic imaging apparatus such as a digital camera, a digital video camera, and a mobile phone device having an imaging function.

Additional advantages and modifications will readily occur to those skilled in the art. Therefore, the invention in its broader aspects is not limited to the specific details and representative embodiments shown and described herein. Accordingly, various modifications may be made without departing from the spirit or scope of the general inventive concept as defined by the appended claims and their equivalents.

What is claimed is:

1. An imaging module comprising:
a hollow lens holder open at both ends;
a lens assembled in the lens holder and collecting light input from one end of the lens holder;
a hollow imaging holder having an opening into which the light output from the lens is input;
an optical member assembled in the imaging holder and transmitting or deflecting the light input from one end of the imaging holder; and
an image sensor assembled in the imaging holder and having a light-receiving region formed on a surface, the light-receiving region being configured to receive the light transmitted or deflected by the optical member and to perform photoelectric conversion of the received light; wherein
a shape of an opening of a light-output-side end portion of the lens holder and a shape of a light-input surface of the optical member are the same shape, and by fitting the light-output-side end portion of the lens holder and the imaging holder to each other, an inner circumferential surface of the lens holder and an outer circumferential surface of the optical member are directly fitted to each other, a position of a part of an outer circumferential surface of the light-output-side end portion of the lens holder is further defined by being in contact with a part of an inner circumferential surface of the imaging holder, and an optical axis center of the lens and a center of the light to be received by the light-receiving region of the image sensor are aligned with each other;
a protrusion portion is formed on the light-input surface of the optical member, the size of the protrusion portion coinciding with an inner circumferential surface of the light-output-side end portion of the lens holder, and
the optical axis center of the lens and the center of the light to be received by the light-receiving region of the image sensor are aligned with each other by fitting the inner circumferential surface of the light-output-side end portion of the lens holder to a circumferential surface of the protrusion portion of the optical member, and a position of the light-output-side end portion of the lens holder in an axial direction is defined by causing a distal end to meet the light-input surface of the optical member.

2. The imaging module according to claim 1, wherein marks for identifying a position of each holder in an axial direction are respectively put on an outer circumferential surface of the lens holder and an outer circumferential surface of the imaging holder.

3. The imaging module according to claim 1, wherein the imaging module is incorporated in a distal end portion of an endoscope apparatus to be inserted into a living body.

4. The imaging module according to claim 1, wherein the imaging module is incorporated in a distal end portion of an endoscope apparatus to be inserted into a living body.

* * * * *